US011583262B2

(12) United States Patent
DeHeer

(10) Patent No.: US 11,583,262 B2
(45) Date of Patent: Feb. 21, 2023

(54) RETRACTOR

(71) Applicant: DeHeer Orthopedics LLC, Westfield, IN (US)

(72) Inventor: Patrick A. DeHeer, Westfield, IN (US)

(73) Assignee: DeHeer Orthopedics LLC, Westfield, IN (US)

( * ) Notice: Subject to any disclaimer, the term of this patent is extended or adjusted under 35 U.S.C. 154(b) by 77 days.

(21) Appl. No.: 16/717,551

(22) Filed: Dec. 17, 2019

(65) Prior Publication Data

US 2020/0187929 A1    Jun. 18, 2020

Related U.S. Application Data

(60) Provisional application No. 62/781,465, filed on Dec. 18, 2018.

(51) Int. Cl.
*A61B 17/02* (2006.01)

(52) U.S. Cl.
CPC ...... *A61B 17/0206* (2013.01); *A61B 17/0218* (2013.01); *A61M 2210/086* (2013.01)

(58) Field of Classification Search
CPC .. A61B 17/0218; A61B 17/02; A61B 17/0206
See application file for complete search history.

(56) References Cited

U.S. PATENT DOCUMENTS 4,702,230 A    10/1987 Pelta
5,669,914 A    9/1997 Eckhoff
(Continued)

FOREIGN PATENT DOCUMENTS

EP    1117335    3/2009
WO    2014137390    9/2014

OTHER PUBLICATIONS

"Retractor Portfolio," Symmetry Surgical, symmetrysurgical.com, Jun. 27, 2015. https://web.archive.org/web/20150627064852/http://www.symmetrysurgical.com/Documents/PDF/Retractors_Symmetry%20Surgical%20Catalog%20Digital_v2.pdf.
(Continued)

*Primary Examiner* — Eduardo C Robert
*Assistant Examiner* — Michelle C Eckman
(74) *Attorney, Agent, or Firm* — Faegre Drinker Biddle & Reath LLP

(57) ABSTRACT

A surgical retractor adapted to develop the interval between the gastrocnemius and soleus to facilitate one or both of gastrocnemius and soleus recession to treat equinus is disclosed. Particular forms of the present disclosure include a retractor having handles extending transversally to the retractor head such that the handles may be used to manipulate and actuate the instrument with its head positioned through an incision and into the interval between the gastrocnemius and soleus, with the handles extending either distally or proximally from the incision site so that such handles do not interfere with the surgical procedure. In other illustrative embodiments, the retractor head can include a gastrocnemius retractor and a soleus retractor, each of which include a plurality of guides operable to guide the incision of the fascial layer of the gastrocnemius and soleus, respectively, to effect intermuscular fascial lengthening to relieve equinus. In further illustrative embodiments, ramped guide surfaces may cooperate with a scalpel to vary the depth of the fascial incision along its length. Concave outwardly facing surfaces of the retractor head may, in certain embodiments, be utilized to cup the gastrocnemius and soleus during the procedure.

25 Claims, 16 Drawing Sheets

(56) References Cited

U.S. PATENT DOCUMENTS

| | | | |
|---|---|---|---|
| 5,688,282 A | 11/1997 | Baron et al. | |
| 6,042,540 A | 3/2000 | Johnston et al. | |
| 6,056,754 A | 5/2000 | Haines et al. | |
| D448,080 S | 9/2001 | Moscarelli et al. | |
| 6,309,349 B1 | 10/2001 | Bertolero et al. | |
| 6,663,562 B2 | 12/2003 | Chang | |
| 7,141,015 B2 | 11/2006 | Ruane | |
| 7,276,024 B1 | 10/2007 | Royse et al. | |
| 7,481,766 B2 | 1/2009 | Lee et al. | |
| 7,789,885 B2 | 9/2010 | Metzger | |
| 7,988,625 B2 | 8/2011 | Abdelgany et al. | |
| 8,062,217 B2 | 11/2011 | Boucher et al. | |
| 8,262,571 B2 | 9/2012 | Ritland | |
| 8,366,712 B2 * | 2/2013 | Bleich | A61B 17/32053 606/79 |
| 8,398,641 B2 * | 3/2013 | Wallace | A61B 17/864 606/79 |
| D679,395 S | 4/2013 | Wright et al. | |
| 8,430,881 B2 * | 4/2013 | Bleich | A61B 17/1659 606/84 |
| 8,568,416 B2 * | 10/2013 | Schmitz | A61B 17/7068 606/79 |
| 8,585,704 B2 * | 11/2013 | Schmitz | A61B 17/1671 606/177 |
| 8,652,138 B2 * | 2/2014 | Bleich | A61B 17/1659 606/85 |
| 8,876,859 B2 | 11/2014 | Buehler et al. | |
| 8,926,618 B2 | 1/2015 | Collazo | |
| 9,084,591 B2 | 7/2015 | Reglos et al. | |
| 9,095,301 B2 | 8/2015 | Hamada | |
| 9,271,711 B2 | 8/2016 | Hawkins et al. | |
| 9,408,596 B2 | 8/2016 | Blain | |
| 9,433,405 B2 | 9/2016 | Ott et al. | |
| 9,498,198 B2 | 11/2016 | Hu et al. | |
| 9,498,199 B2 | 11/2016 | Colquhoun et al. | |
| 9,549,723 B2 | 1/2017 | Hynes et al. | |
| 9,585,649 B2 | 3/2017 | Blain et al. | |
| 9,693,763 B2 | 7/2017 | Blain | |
| D797,930 S | 9/2017 | Khaw | |
| 2002/0147387 A1 | 10/2002 | Paolitto et al. | |
| 2007/0299315 A1 | 12/2007 | Geller | |
| 2009/0192511 A1 | 7/2009 | Haffenreffer | |
| 2010/0022845 A1 | 1/2010 | Ott et al. | |
| 2012/0296172 A1 | 11/2012 | Raven et al. | |
| 2013/0231538 A1 * | 9/2013 | Guilford | A61B 17/02 600/210 |
| 2016/0192922 A1 | 7/2016 | Friedrich et al. | |
| 2016/0287236 A1 | 10/2016 | Garcia-Bengochea et al. | |
| 2017/0007225 A1 | 1/2017 | Ferro et al. | |
| 2017/0042526 A1 | 2/2017 | Trimarche | |
| 2017/0049462 A1 | 2/2017 | Walton | |
| 2017/0095240 A9 | 4/2017 | Waugh et al. | |
| 2017/0095241 A1 * | 4/2017 | Perler | A61B 90/30 |
| 2017/0281213 A1 * | 10/2017 | Early | A61B 17/320016 |
| 2018/0085133 A1 | 3/2018 | Lavallee et al. | |
| 2019/0038273 A1 * | 2/2019 | Perler | A61B 17/02 |

OTHER PUBLICATIONS

"Weitlaner-Beckmanm Self-Retaining Retractor 3x4 Prongs 22cm," Scatter, scatterinstruments.com, accessed: Apr. 2018. http://store.scatterinstruments.com/weitlaner-beckmanm-self-retaining-retractor-3x4-prongs-22cm-33-042-01.html.

"Henly (Modified) Retractor System—Retractor frame w/3 sets of removable blades & 3 removable center blades, Stainless Steel, 7" (17.5cm)," Wexler Surgical, wexlersurgical.com, Item No. TL0130.1, Apr. 20, 2018. https://web.archive.org/web/20180420004930/https://www.wexlersurgical.com/henly-modified-retractor-system-retractor-frame-w3-sets-of-removable-bladesremovable-center-blades-stainless-steel-7quot-175cm-p-2452.html?type=search-specialty.

"Cone Laminectomy Retractor," Alibaba, alibaba.com, Model No. L50-08061, Apr. 20, 2010. https://web.archive.org/web/20180420003741/https://www.alibaba.com/product-detail/Cone-laminectomy-Retractor_50037958393.html?spm=a2700.7724857.main07.35.6b3c14fflYG4ls.

* cited by examiner

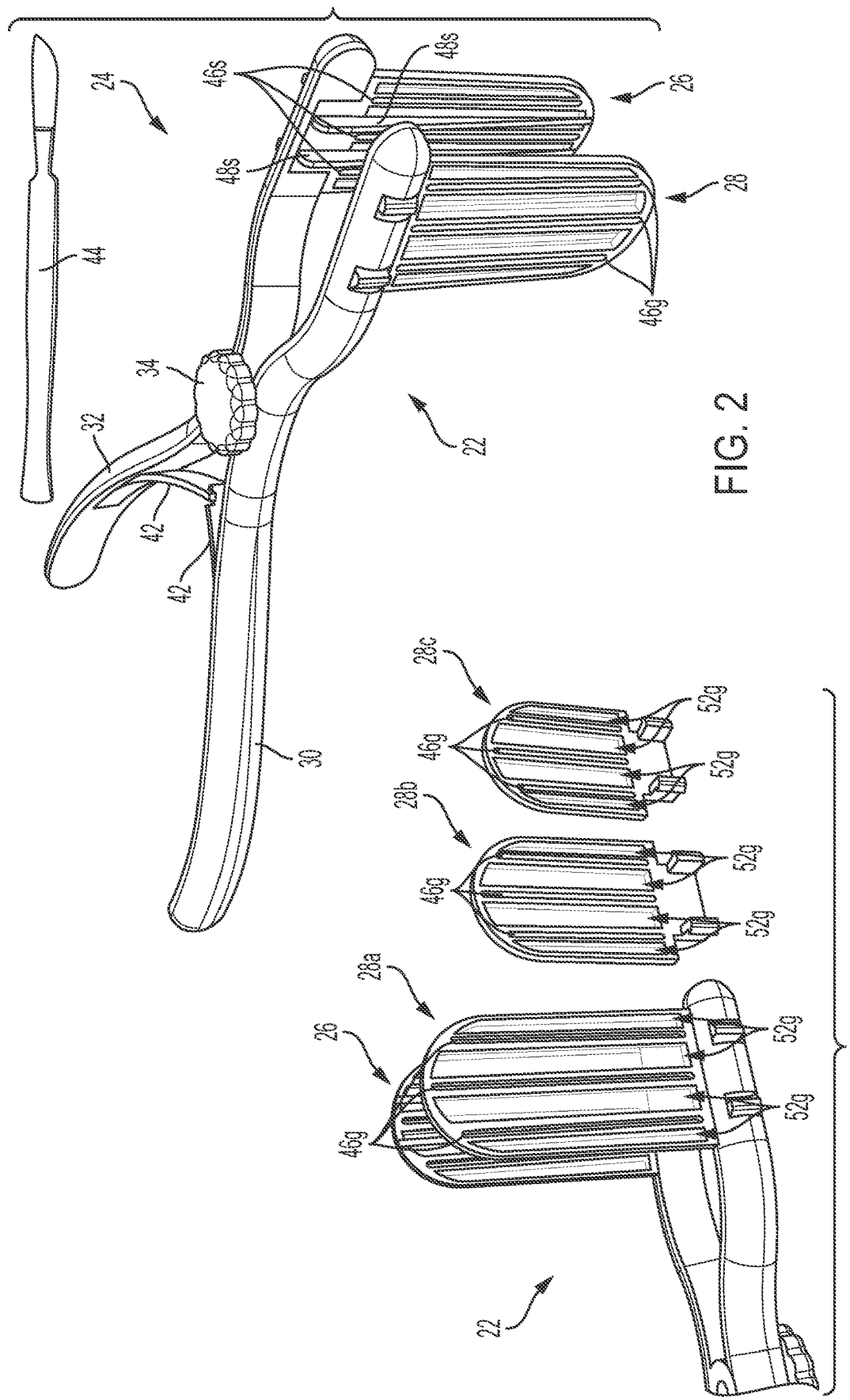

RETRACTOR

CROSS-REFERENCE TO RELATED APPLICATIONS

The present application claims the benefit of U.S. Provisional Patent Application Ser. No. 62/781,465, filed on Dec. 18, 2018, the complete disclosure of which is expressly incorporated by reference herein.

BACKGROUND OF THE DISCLOSURE

1. Field of the Disclosure

This disclosure relates generally to a retractor for use in surgical procedures and, more specifically, to a retractor particularly suited for spacing the gastrocnemius and soleus to facilitate a recession of one or both of the gastrocnemius and soleus to effect an intermuscular fascial lengthening to relieve equinus.

2. Description of the Related Art

Talipes equinus or simply equinus is a condition in which the upward bending motion of the ankle joint (dorsiflexion) is limited. Equinus can be defined as the inability to achieve ankle joint dorsiflexion of less than 90 degrees relative to the distal leg. Equinus can be due to tightness in the calf muscles, i.e., the gastrocnemius and/or the soleus.

A number of non-invasive treatments can be utilized in an attempt to counteract equinus, including stretching exercises, the use of orthotics, as well as a variety of night splints and braces. If a patient does not respond to such conservative care, then a surgical procedure to effect gastrocnemius and/or soleus lengthening can be utilized. Particularly, a gastrocnemius recession, i.e., an incision of the gastrocnemius fascial layer from lateral to medial can be utilized either together with or in lieu of a similar soleus recession, i.e., incision of the fascial layer of the soleus from lateral to medial. When performing such intramuscular fascial lengthening to relieve equinus, the gastrocnemius and soleus are typically spaced from one another using conventional retractors. For example, an anal speculum is often utilized to retract the gastrocnemius from the soleus. Such conventional retractors are not particularly well-suited to the task at hand.

What is needed in the art is a surgical retractor particularly adapted for use in a gastrocnemius and/or soleus recession and an associated surgical technique.

SUMMARY OF THE DISCLOSURE

The present disclosure provides a surgical retractor adapted to develop the interval between the gastrocnemius and soleus to facilitate one or both of gastrocnemius and soleus recession to treat equinus. Particular forms of the present disclosure include a retractor having handles extending transversally to the retractor head such that the handles may be used to manipulate and actuate the instrument with its head positioned through an incision and into the interval between the gastrocnemius and soleus, with the handles extending either distally or proximally from the incision site so that such handles do not interfere with the surgical procedure. In other illustrative embodiments, the retractor head can include a gastrocnemius retractor and a soleus retractor, each of which include a plurality of guides operable to guide the incision of the fascial layer of the gastrocnemius and soleus, respectively, to effect intermuscular fascial lengthening to relieve equinus. In further illustrative embodiments, ramped guide surfaces may cooperate with a scalpel to vary the depth of the fascial incision along its length. Concave outwardly facing surfaces of the retractor head may, in certain embodiments, be utilized to cup the gastrocnemius and soleus during the procedure. Additional exemplifications of the present disclosure may embody the previously described surgical retractor in combination with aspects of a conventional Chung retractor.

The present disclosure, in one form thereof, provides a method of relieving equinus, comprising: incising a patient's skin to provide an access to a gastrocnemius and a soleus of the patient; inserting an instrument into the access, the instrument comprising a retractor head, the retractor head comprising: a soleus retractor; a gastrocnemius retractor, the gastrocnemius retractor moveable relative to the soleus retractor over a range of motion from a closed position to an open position, the retractor head sized and shaped to be positioned in an interval between the gastrocnemius and the soleus in the closed position, at least one of the gastrocnemius retractor and the soleus retractor comprising a plurality of spaced guides; the inserting step further comprising inserting the retractor head into the access and into the interval between the gastrocnemius and the soleus; spacing the gastrocnemius from the soleus along a sagittal axis by opening the retractor head to space the soleus retractor from the gastrocnemius retractor; and guiding, with a first one of the plurality of spaced guides, a first recession of one of the gastrocnemius and the soleus to effect a first intramuscular fascial lengthening to relieve equinus.

The present disclosure, in another form thereof, provides an instrument for facilitating a recession to effect an intramuscular fascial lengthening to relieve equinus, the instrument comprising: a retractor head, comprising: a soleus retractor; a gastrocnemius retractor, the gastrocnemius retractor moveable relative to the soleus retractor over a range of motion from a closed position to an open position, the retractor head sized and shaped to be positioned through an incision through a patient's skin providing an access to a gastrocnemius and a soleus of the patient and into an interval between the gastrocnemius and the soleus in the closed position; a first handle, the soleus retractor extending from the first handle; a second handle, the gastrocnemius retractor extending from the second handle, the first handle moveably secured to the second handle so that actuation of the first handle relative to the second handle actuates the soleus retractor relative to the gastrocnemius retractor over the range of motion; the gastrocnemius retractor comprising a plurality of spaced guide slots, each of the plurality of spaced guide slots sized, shaped and positioned to guide a gastrocnemius recession to effect the intramuscular fascial lengthening to relieve equinus when the retractor head is positioned in the interval between the soleus and the gastrocnemius.

In an additional form thereof, the present disclosure provides an instrument for facilitating a recession to effect an intramuscular fascial lengthening to relieve equinus, the instrument comprising: a retractor head, comprising: a soleus retractor; a gastrocnemius retractor, the gastrocnemius retractor moveable relative to the soleus retractor over a range of motion from a closed position to an open position, the retractor head sized and shaped to be positioned through an incision through a patient's skin providing an access to a gastrocnemius and a soleus of the patient and into an interval between the gastrocnemius and the soleus in the closed position; a first handle, the soleus retractor extending from the first handle; a second handle, the gastrocnemius retractor extending from the second handle, the first handle moveably secured to the second handle so that actuation of the first handle relative to the second handle actuates the soleus retractor relative to the gastrocnemius retractor over the range of motion; the first handle extending transversely from the soleus retractor, the second handle extending transversely from the gastrocnemius retractor such that, with the soleus retractor and the gastrocnemius retractor positioned in the interval between the gastrocnemius and the soleus, each of the first handle and the second handle extend one of distally and proximally away from the incision; the gastrocnemius retractor comprising a plurality of spaced guides, each of the plurality of spaced guides sized, shaped and positioned to guide a gastrocnemius recession to effect the intramuscular fascial lengthening to relieve equinus when the retractor head is positioned in the interval between the soleus and the gastrocnemius, each of the spaced guides spaced a non-adjustable distance from the other of the spaced guides, whereby actuation of the first handle relative to the second handle does not affect the spacing of the plurality of spaced guides of the gastrocnemius retractor.

BRIEF DESCRIPTION OF THE DRAWINGS

The above-mentioned and other features and advantages of this disclosure, and the manner of attaining them, will become more apparent and will be better understood by reference to the following description of exemplary embodiments taken in conjunction with the accompanying drawings, wherein:

FIG. 1 is a partial, perspective, exploded view of an embodiment of the retractor of the present disclosure, illustrating alternative retractor head attachments;

FIG. 2 is an exploded, perspective view of an instrument set in accordance with an embodiment of the present disclosure, the instrument set including a retractor in accordance with the present disclosure and a scalpel;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION OF THE DRAWINGS

Figure 3:
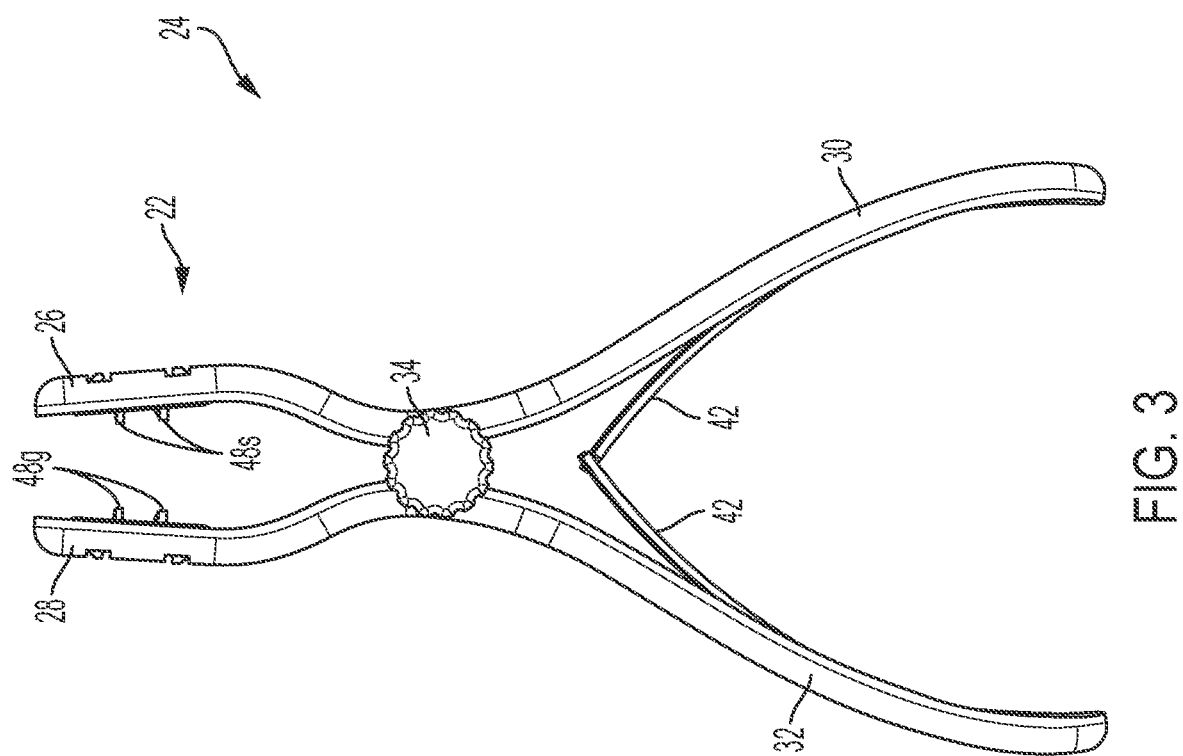
FIG. 3 is a top plan view of a retractor of the present disclosure.
Figure 4:
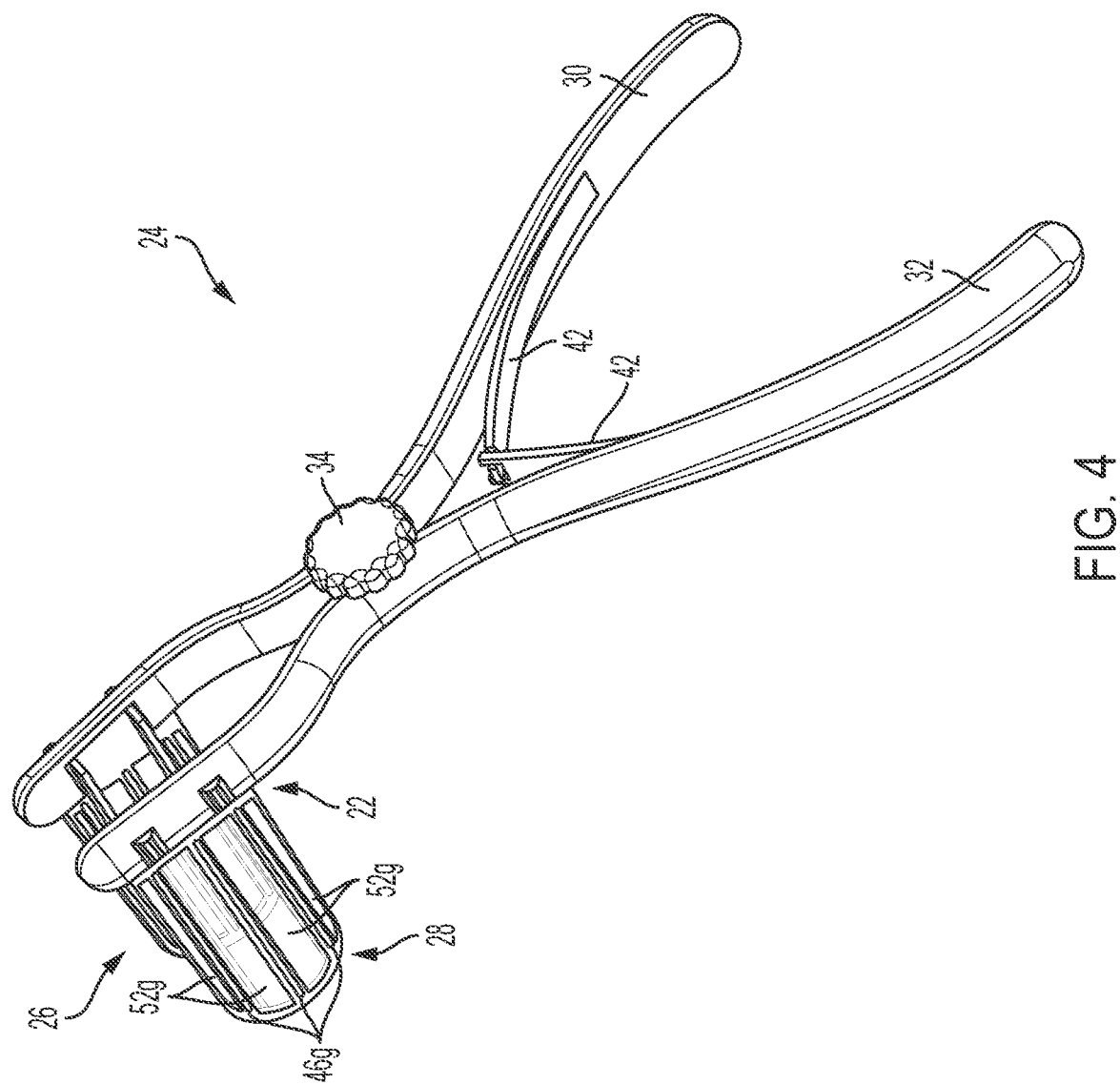
FIG. 4 is a top perspective view of the retractor of FIG. 3.
Figure 5:
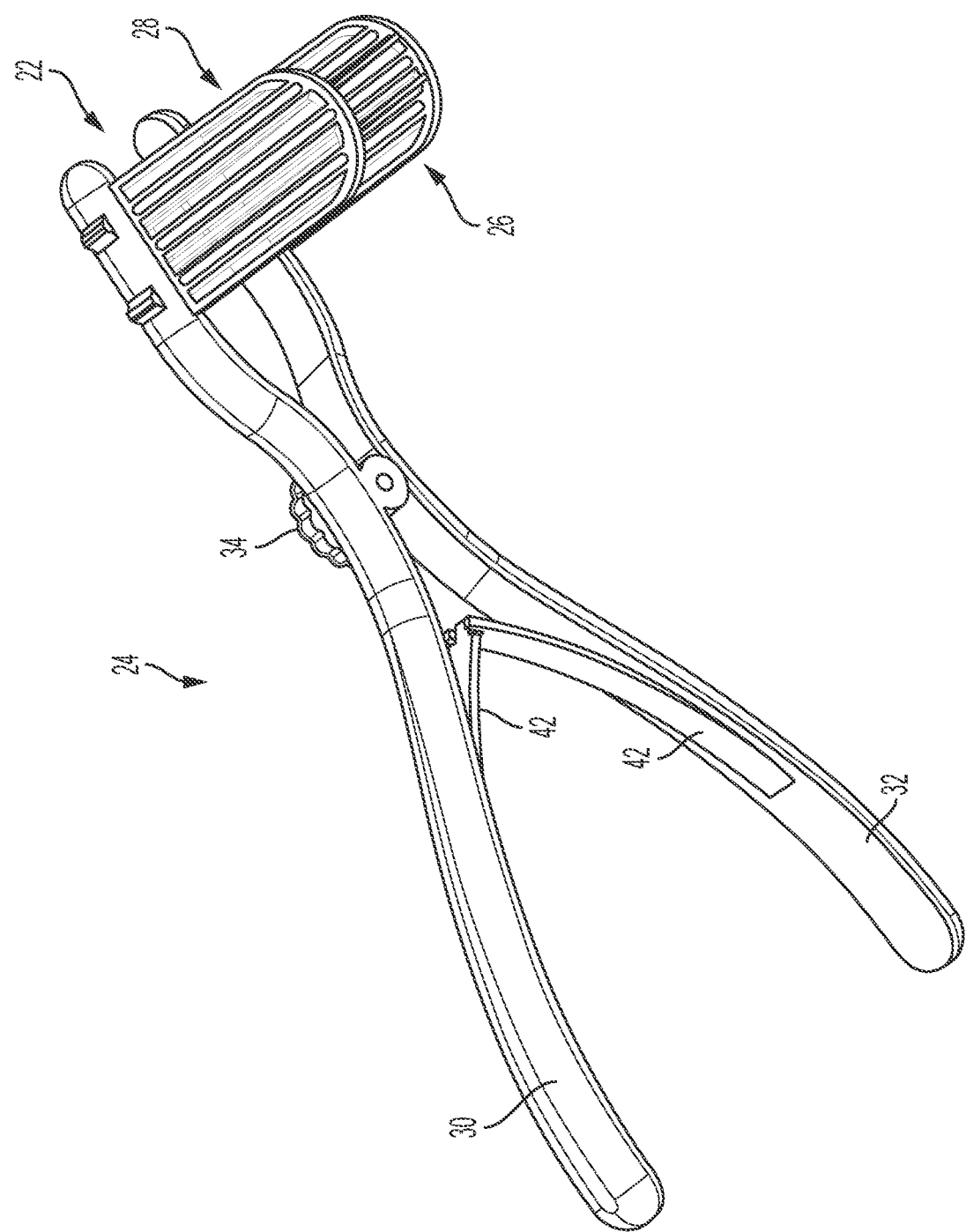
FIG. 5 is a bottom perspective view of the retractor of FIG. 3.

For the purposes of promoting an understanding of the principals of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrative devices and described methods and further applications of the principles of the invention which would normally occur to one skilled in the art to which the invention relates.

Figure 7:
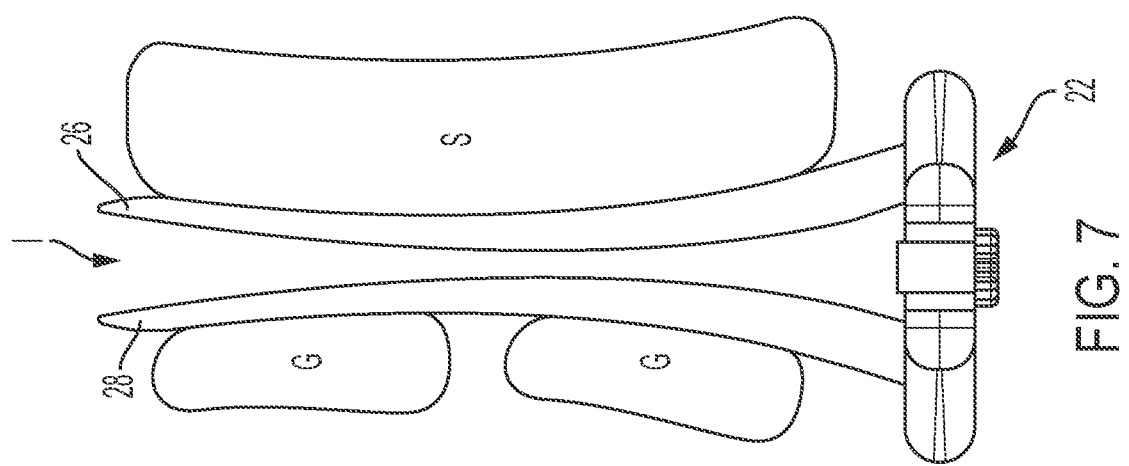
FIG. 7 is a partial schematic view of the retractor head of an exemplary retractor of the present disclosure positioned between the gastrocnemius (G) and soleus (S) of a patient.
Figure 8:
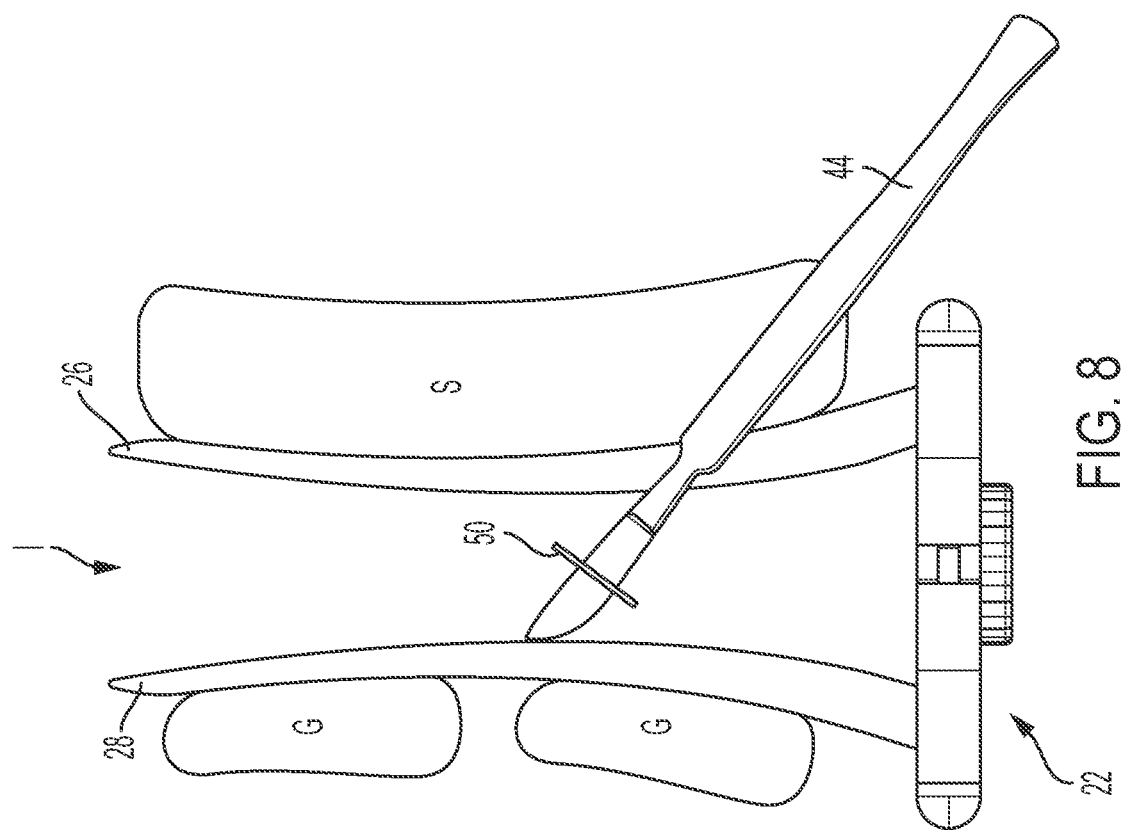
FIG. 8 is partial schematic view similar to FIG. 7, but with the retractor head actuated to distract the soleus (S) from the gastrocnemius (G)

The present disclosure provides an instrument and associated method of relieving equinus. Specifically, the present disclosure provides a retractor insertable into the interval between the gastrocnemius and the soleus to facilitate an intramuscular fascial lengthening of one or both of the gastrocnemius and the soleus to relieve equinus. As shown in FIGS. 7 and 8, the gastrocnemius features a medial head and a lateral head and is positioned posterior of the soleus. As is known by those of skill in this art, the gastrocnemius and soleus join in the Achilles tendon distally.

To relieve equinus, an incision can be made in the fascial layer of one or both of the soleus and gastrocnemius to allow for a lengthening of such structure to facilitate further dorsiflexion of the ankle joint. The procedure begins with the patient in a supine position, with standard prepping and draping to above the knee. Typically, a thigh tourniquet is utilized. The surgical approach begins with a medial calf incision 20 (FIG. 9) started approximately 2 finger breadths below the anterior boarder of the tibia, just above the myotendinous junction. The incision is typically 4-6 centimeters in length and is made just through the skin using, e.g., a number 10 blade. The incision is then deepened with Metzenbaum scissors to the level of deep fascia. If the great saphenous vein or saphenous nerve are encountered, they should be retracted anteriorly. Digital blunt dissection is then utilized to expose the deep fascia overlying the gastrocnemius and soleus muscles. A self-retaining retractor, such as a Weitlander or Chung retractor can then be inserted to expose the deep fascia overlying the gastrocnemius and soleus muscles. In embodiments incorporating features of the Chung/Weitlander retractor such as instrument 24''' illustrated in FIG. 13, the instrument of the present disclosure can be utilized in lieu of a separate, additional retractor. At this point, the surgeons index finger can be utilized to identify the intramuscular interval I (FIG. 7) between the gastrocnemius G and soleus S muscles. It is critical at this junction to avoid creating a false plane within one of the muscles by using excessive force.

Figure 9:
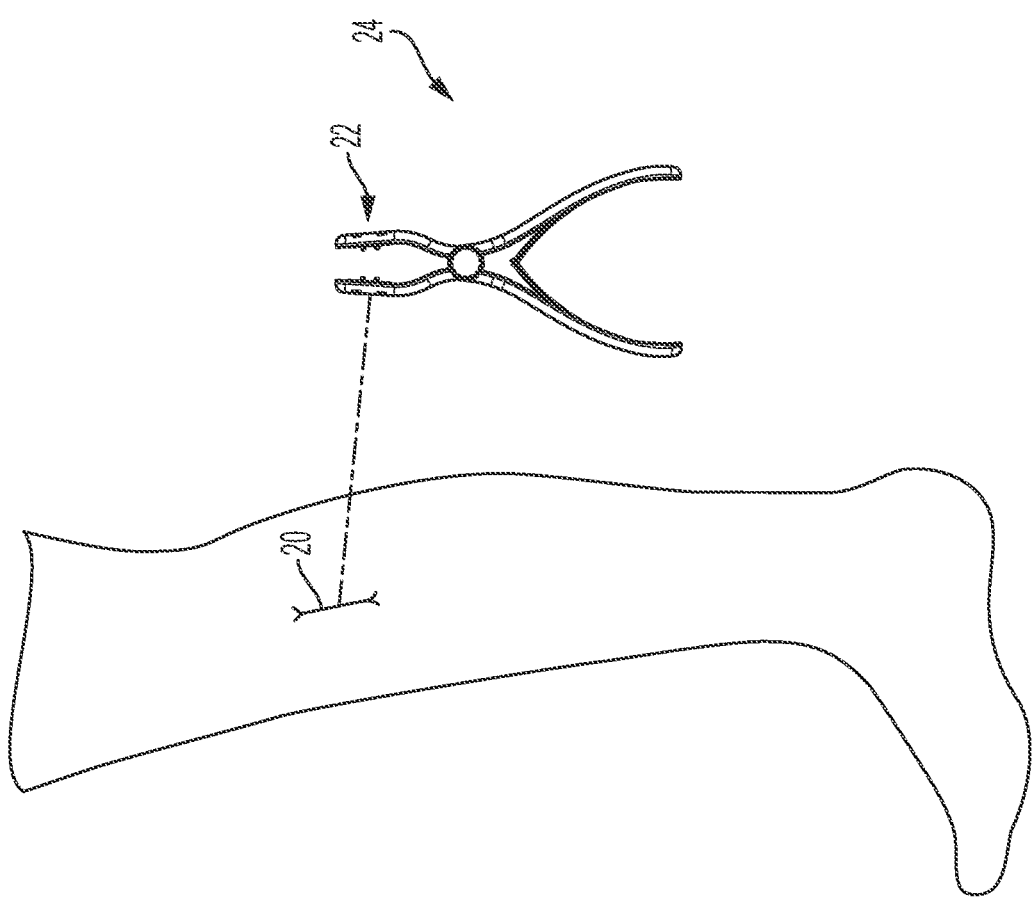
FIG. 9 is a partial, exploded view of a retractor of the present disclosure and the lower leg of a patient.

At this point of the surgical procedure, instrument 24, is utilized to facilitate recession of the gastrocnemius G and/or soleus S. Referring to the figures, instrument 24 includes retractor head 22 featuring soleus retractor 26 and gastrocnemius retractor 28, with first handle 30 and second handle 32 extending transversely therefrom. As illustrated in FIG. 9, after forming incision 20 and proceeding to this point of the surgical technique, retractor head 22 is inserted into the access through incision 20. Particularly, retractor head 22 is inserted between the gastrocnemius (posterior) and soleus (anterior) muscle bellies to expose the fascia layers of both muscles. The fascia layer is superior the conjoined aponeurosis of the muscles.

Referring to the figures, instrument 24 includes first handle 30 and second handle 32. As illustrated, first handle 30 is movably secured to second handle 32. Specifically, referring to FIG. 6, thumbscrew 34 is secured through yoke 36 of first handle 30 and pivot 38 of second handle 32 to pivotally secure first handle 30 to second handle 32. In construction of instrument 24, pivot 38 of second handle 32 is positioned intermediate the uprights of yoke 36. In one exemplification, a threaded shaft extends from thumbscrew 34 and, in construction, is threadedly engaged with one of the uprights of yoke 36 and positioned through a central aperture the other upright of yoke 36 and pivot 38. Intermediate the threaded end of the shaft extending from thumbscrew 34 and thumbscrew 34 is an unthreaded shaft about which pivot 38 can rotate to actuate instrument 24 between open and closed positions. Thumbscrew 34 can be positioned in a rotate position in which pivot 38 is freely rotatable between the uprights of yoke 36. Thumbscrew 34 can also be positioned in a lock position in which pivot 38 is locked relative to yoke 36 to prevent movement of first handle 30 relative to second handle. In the rotate position, pivot 38 is freely rotatable about the unthreaded shaft portion extending from thumbscrew. To move from the rotate position to the lock position, thumbscrew 34 is rotated to thread the shaft extending therefrom further into yoke 36 and thereby force the uprights of yoke 36 toward each other and into frictional engagement with pivot 38.

First handle 30 and second handle 32 each extend opposite retractor head 22 and transversely from gastrocnemius retractor 28 and soleus retractor 26. More specifically, in the exemplification illustrated, gastrocnemius retractor 28 and soleus retractor 26 extend orthogonally from the ends of first handle 30 and second handle 28 distal of the surgeon during use of instrument 24. In use, first handle 30 and second handle 32 may be grasped by a surgeon and manipulated in the surgical technique as described herein. In particular embodiments of the present disclosure, the ends of first handle 30 and second handle 32 opposite retractor head 22, i.e., the ends of first handle 30 and second handle 32 grasped and actuated by the surgeon during use of instrument 24, may be knurled or otherwise surface treated to facilitate grasping of the instrument by a surgeon's gloved hand in a surgical environment.

First handle 30 and second handle 32 can be actuated about pivot axis 40 by moving first handle 30 and second handle 32 relative to one another. Particularly, first handle 30 and second handle 32 can be moved closer to each other to spread gastrocnemius retractor 28 and soleus retractor further from one another. A spring 42 extends from each of first handle 30 and second handle 32, with both springs coming together as illustrated, e.g., in FIGS. 2-5 to bias first handle 30 and second handle 32 away from one another. In the biased position, retractor head 22 of instrument 24 maintains a closed position, with soleus retractor 26 and gastrocnemius retractor 28 being positioned as close to one another as the structures of instrument 24 will allow. In FIGS. 1-5, this closed position is illustrated with gastrocnemius retractor 28 spaced from soleus retractor 26; however, the closed position may comprise a position in which gastrocnemius retractor 28 abuts soleus retractor 26. Generally speaking, a "closed" position of instrument denotes a position with gastrocnemius retractor 28 positioned closer to soleus retractor 26 than in an "open" position and vice versa.

Figure 10:
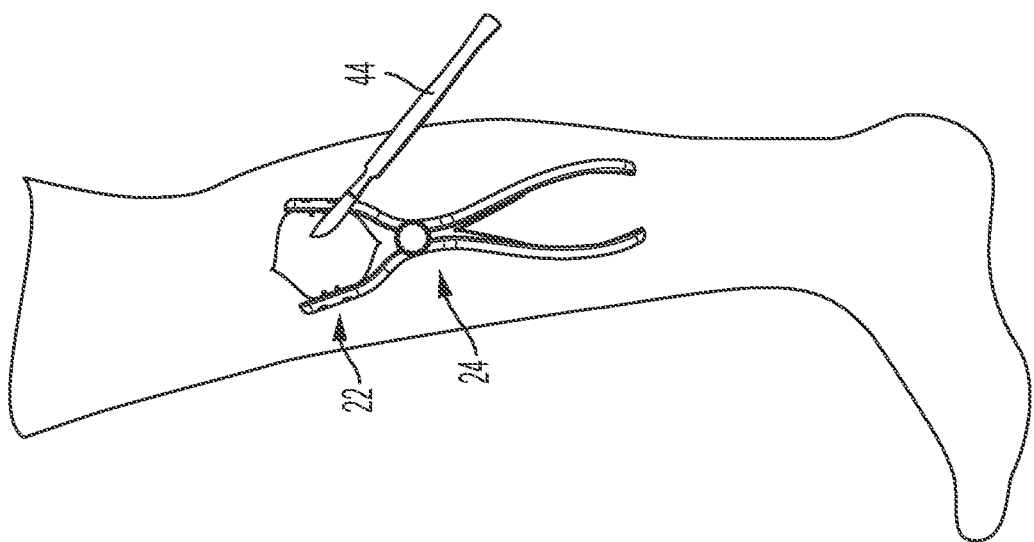
FIG. 10 is a partial view of a retractor of the present disclosure inserted into an incision in the lower leg of a patient to access the interval between the gastrocnemius (G) and the soleus (S) to facilitate an intramuscular fascial lengthening to relieve equinus in accordance with the present disclosure.
Figure 11A:
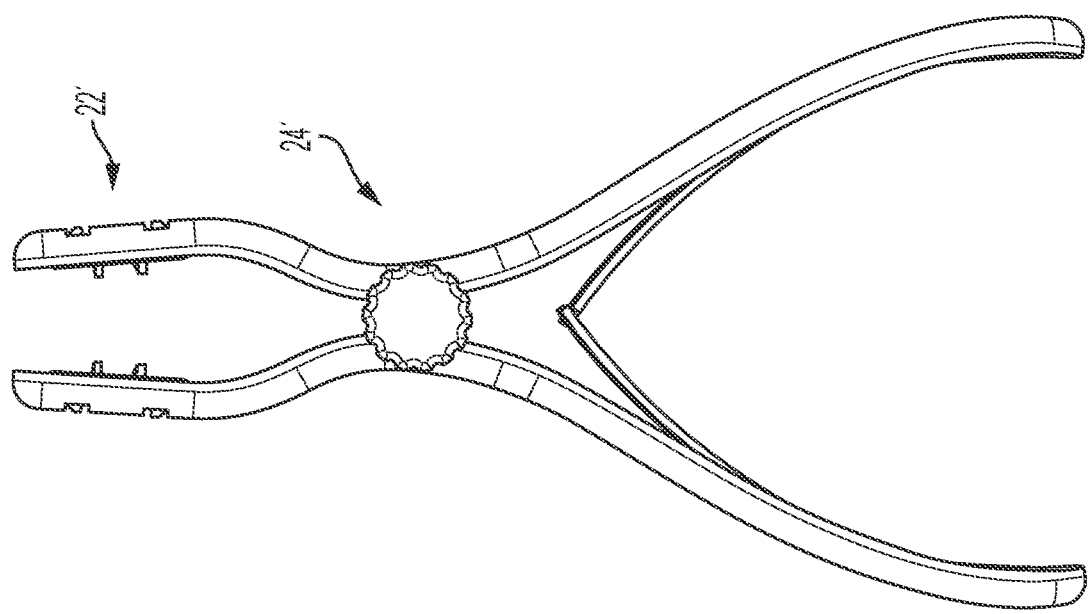
FIGS. 11A-11E illustrate an alternative embodiment instrument 24' in accordance with the present disclosure.
Figure 11B:
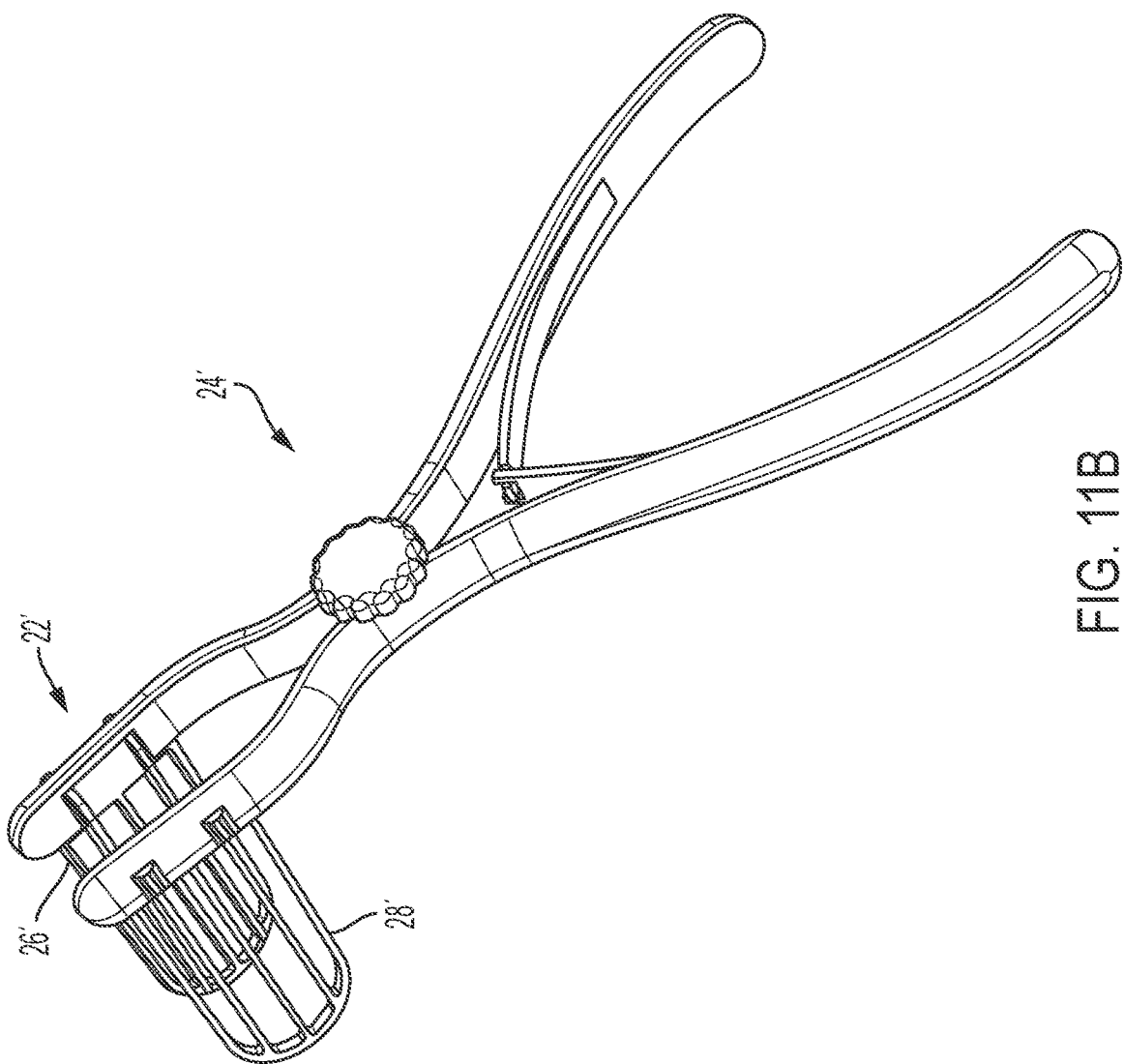
Figure 11C:
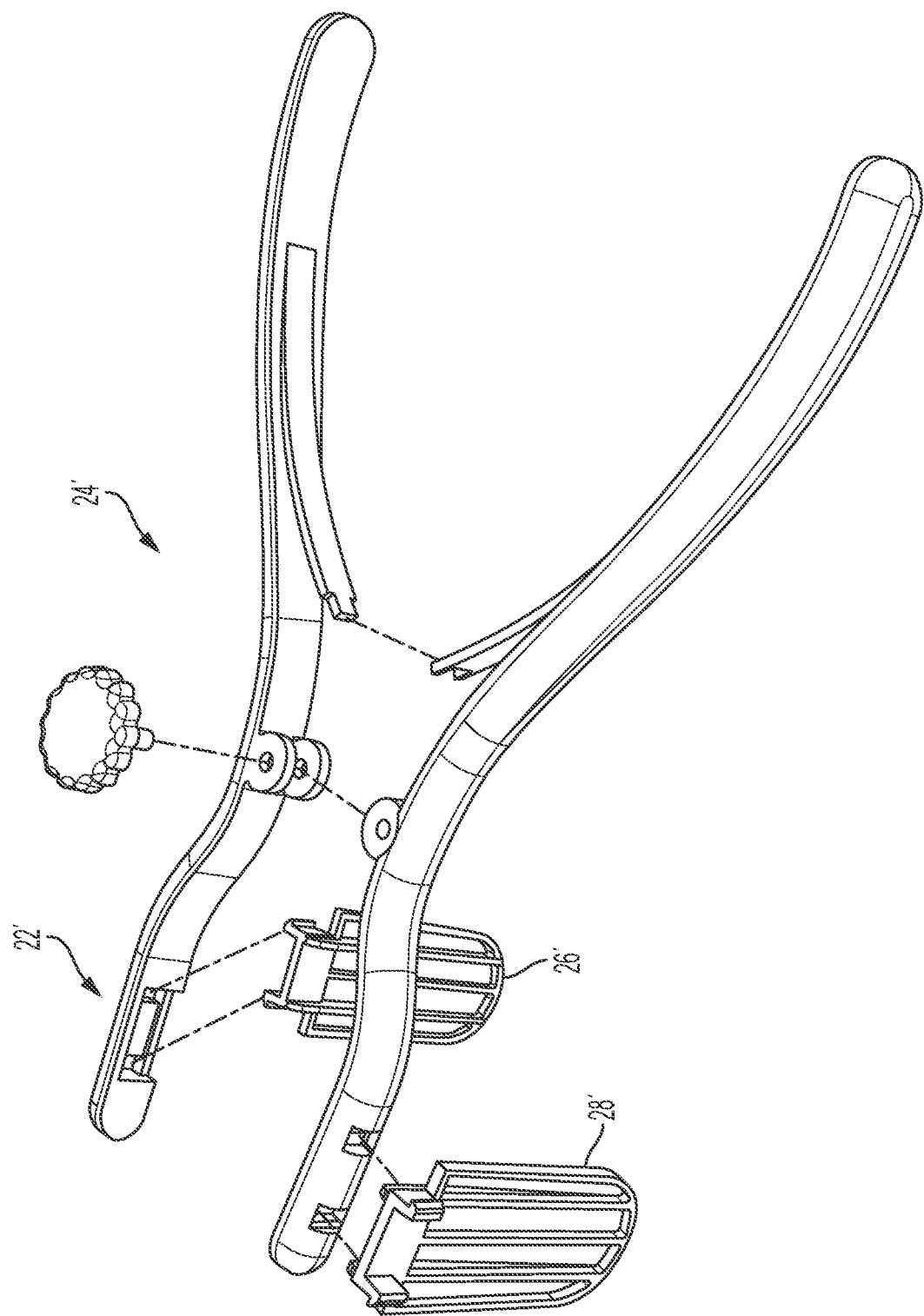
Figure 11D:
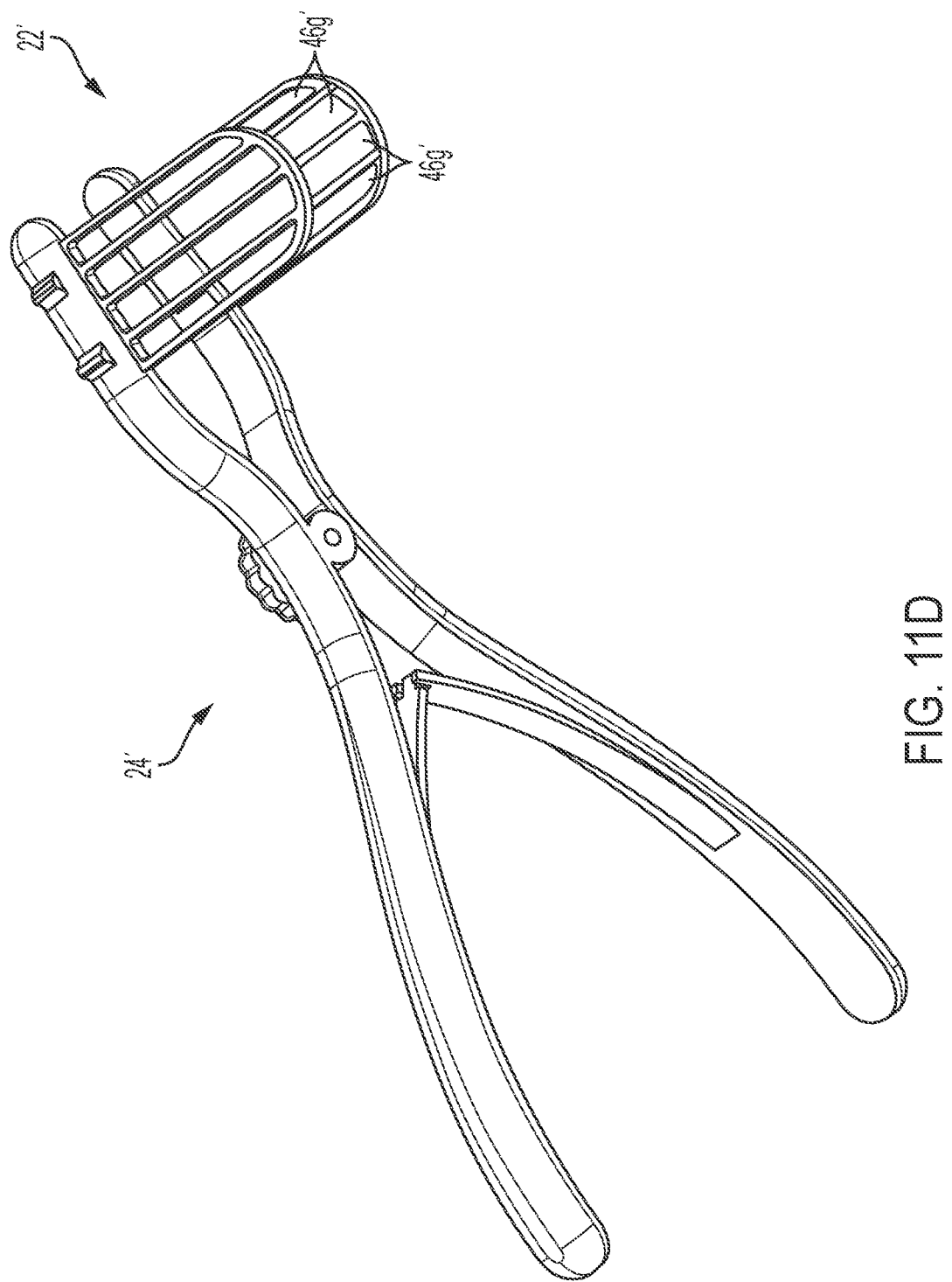
Figure 11E:
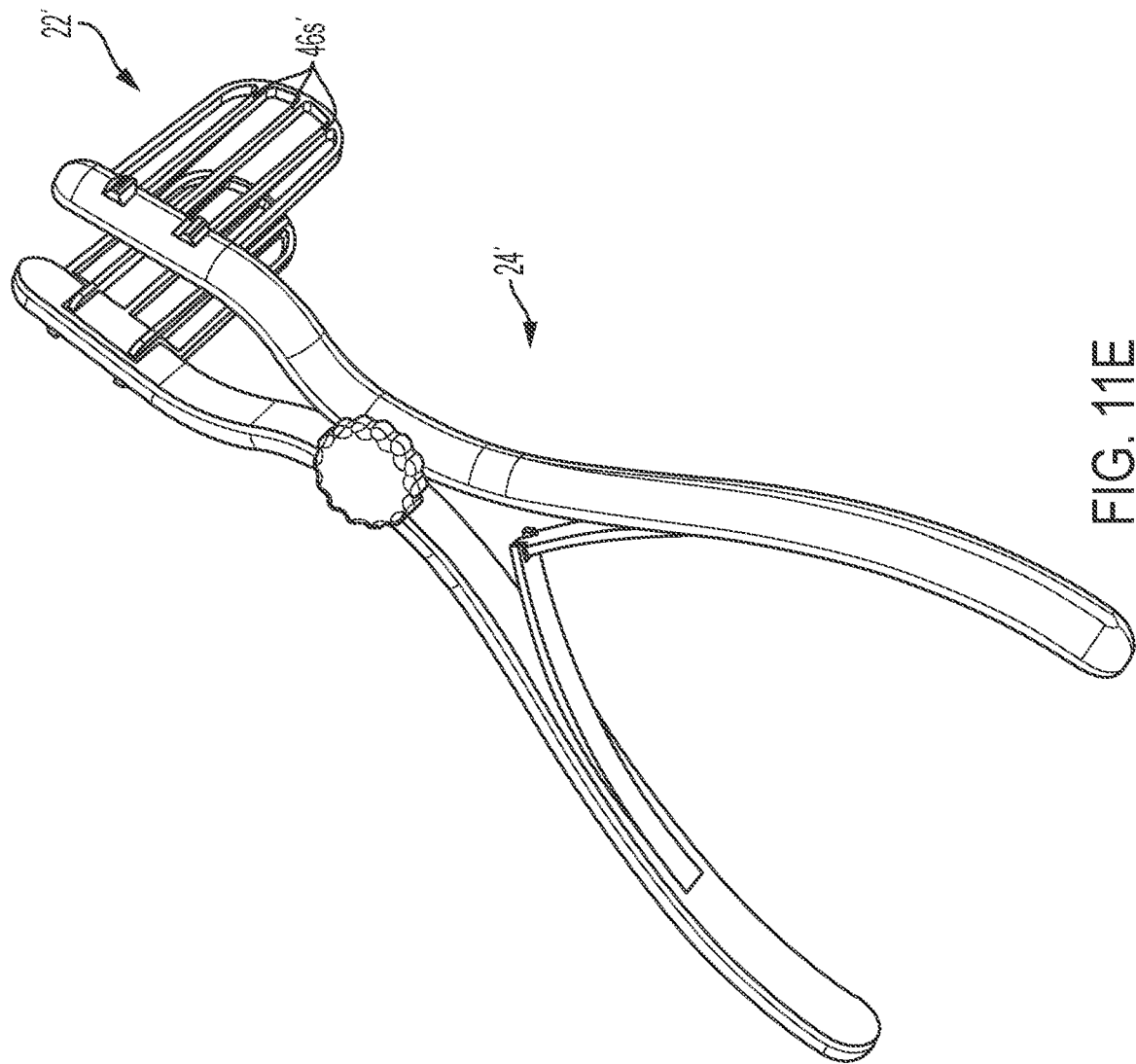

With retractor head 22 positioned in a closed position, the surgeon can manipulate instrument 24 into the position illustrated in FIG. 10. Specifically, a surgeon may grasp one or both of first handle and second handle 32 to position retractor head 22 through the access provided by incision 20 (FIG. 9) and into the interval I between gastrocnemius G and soleus S, as illustrated in FIG. 7. As the instrument is manipulated through the access provided by incision 20, soleus retractor 26 and gastrocnemius retractor 28 are positioned substantially parallel to a coronal anatomical plane of the patient. In this context, "substantially parallel" means within a small deviation (e.g., 5-10 degrees rotated relative to the frontal axis or the longitudinal axis of the patient) of the desired position. As the surgical approach of the present disclosure is a medial surgical approach, it will be clear to a person having ordinary skill in the art that FIGS. 7 and 8 illustrate a left leg, while FIGS. 9 and 10 schematically illustrate the calf muscles of a right leg.

As illustrated in FIGS. 7 and 8, exemplary soleus retractor 26c and gastrocnemius retractor 28c are formed to include an outwardly facing concave surface. With instrument 24 positioned as illustrated in FIG. 10, with retractor head 22 positioned in interval I and between gastrocnemius G and Soleus S, each of the outwardly facing concave surfaces of soleus retractor 26c and gastrocnemius retractor 28c may be positioned adjacent soleus S and gastrocnemius G, respectively. The outwardly facing concave surfaces of soleus retractor 26c and gastrocnemius retractor 28c facilitate retraction of gastrocnemius G and soleus S by cupping the muscles into a position distracted one from the other. Exemplifications of the present disclosure include gastrocnemius retractor 28c and soleus retractor 26c, each of which incorporate the outwardly facing concave surface described herein and depicted in FIGS. 7 and 8. Alternative exemplifications include gastrocnemius retractor 28 and soleus retractor 26, each of which are substantially planar and do not incorporate the described concavity. Throughout this document the gastrocnemius retractor and soleus retractor will be generically referenced with numerals 28 and 26 (without the alphabetic designator "c" to designate the concave surface), it being understood that the concave versions of the gastrocnemius retractor and soleus retractor can be utilized in the same manner as the non-concave versions.

With retractor head 22 inserted between gastrocnemius G and soleus S to expose the facial layers of both muscles as illustrated in FIGS. 7, 8, and 10, scalpel 44 can be utilized to effect gastrocnemius and/or soleus recession, as further described below.

With Instrument 24 positioned such that retractor head 22 is positioned within interval I between gastrocnemius G and soleus S, as illustrated in FIG. 10, first handle 30 and second handle 32 extend distally toward the ankle of the patient, as illustrated in FIG. 10, such that they extend away from the patient access formed by incision 20 through which the gastrocnemius and/or soleus recession will be performed and also extend away from the muscles to be incised (i.e., they do not extend anteriorly toward the soleus or posteriorly toward the gastrocnemius) in alternative exemplary uses of instrument 24, first handle 30 and second handle 32 may extend proximally away from the patient and away from the patient access formed by incision 20 and away from the muscles to be incised. In the exemplary embodiment illustrated, first handle 30 and second handle 32 extend substantially orthogonally from gastrocnemius retractor 28 and soleus retractor 26. In alternative embodiments, first handle 30 and second handle 32 may extend transversely from gastrocnemius retractor 28 and soleus retractor 26 without being orthogonal (i.e., nominally orthogonal) relative thereto. By extending transversely from gastrocnemius retractor 28 and soleus retractor 26, first handle 30 and second handle 32 can extend away from the surgical access so that the surgical access is not encumbered by these aspects of instrument 24. "Transverse" and "orthogonal" and similar geometric designations are made with reference to the longitudinal axes of the referenced components of instrument 24.

With retractor head 22 positioned in interval I, retractor head 22 is opened to space gastrocnemius G from soleus S along a sagittal axis. When a desired open position is obtained, thumbscrew 34 may be actuated to lock the relative position of gastrocnemius retractor 28 relative to soleus retractor 26, as described above. Specifically, first handle 30 and second handle 32 are actuated toward each other to pivot soleus retractor 26 and gastrocnemius retractor 28 about pivot axis 40 to space soleus retractor 26 from gastrocnemius retractor 28 as illustrated, e.g., in FIG. 8. In this position, scalpel 44 can be inserted through the access formed through incision 20 to incise the gastrocnemius facial layer from lateral to medial to effect a first gastrocnemius recession thereby effecting a first intramuscular facial lengthening to relieve equinus. Specifically, the blade of scalpel 44 is inserted through incision 20 from medial to lateral and inserted into one of guides 46g in gastrocnemius retractor 28. The blade of scalpel 44 is thereafter guided by the guide 46g in which it is inserted. Particularly, with instrument 24 positioned to facilitate gastrocnemius recession to effect intramuscular facial lengthening to relieve equinus, first handle 30 and second handle 32 are, e.g., positioned distally as illustrated in FIG. 10 to align gastrocnemius guides 46g substantially parallel to a transverse anatomical plane to facilitate a medial/lateral incision of gastrocnemius G.

Throughout this document, alphabetic designators are utilized to differentiate similar elements otherwise identified with the same numeric designation, but having certain differences. For example, a "g" is utilized to identify an element particularly associated with a gastrocnemius aspect of the disclosed instrument, while an "s" is utilized to identify an element particularly associated with a soleus aspect of the disclosed instrument. For elements including such designators, a reference to the numeric designation without an alphabetic designation should be taken as a description appropriate to all such elements (whether associated with the gastrocnemius or the soleus aspect of the instrument).

Each guide 46g defines a slot formed by upper and lower surfaces spaced to receive the blade of scalpel 44 while maintaining (within an acceptable tolerance), a medial/lateral trajectory of the blade of scalpel 44 as it is moved from lateral to medial to incise the gastrocnemius facial layer. More particularly, each guide 46g forms a slot nominally larger in width than the width of the blade of scalpel 44 (e.g., a 10 blade) of, e.g., about 1-2 millimeters to allow medial to lateral movement of the blade of scalpel 44 while it is positioned in a guide 46g, but while also substantially preventing rotation of scalpel 44 about its longitudinal axis.

Figure 6:
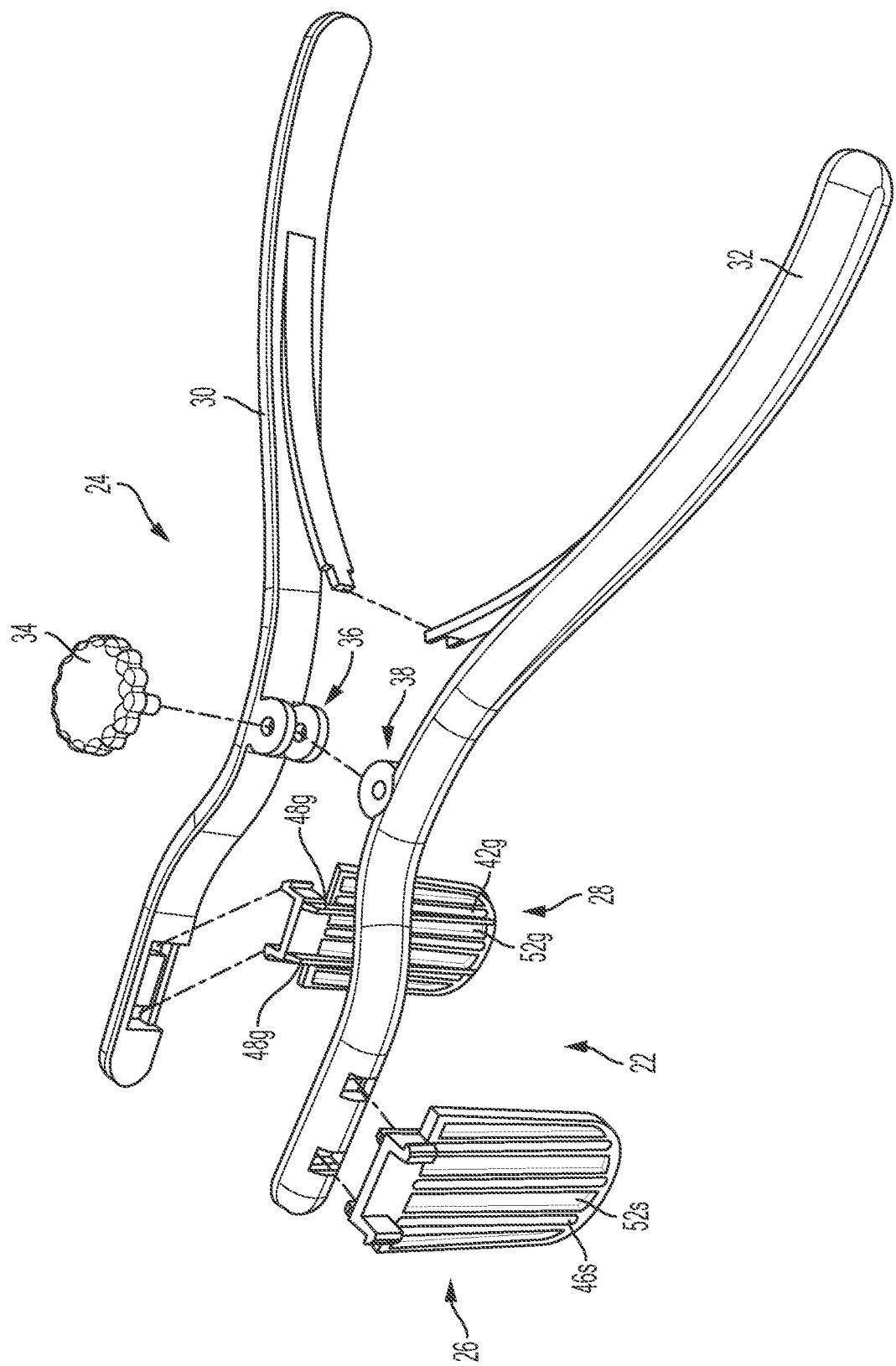
FIG. 6 is an exploded view of the retractor of FIG. 3.

When forming an incision to effect gastrocnemius recession, care must be taken to avoid cutting into the muscle of the gastrocnemius too deeply. Gastrocnemius retractor 28 may incorporate a depth guide positioned to cooperate with scalpel 44 to limit the travel of scalpel 44 through each of guides 46g (with the distal most guide 46g typically used to guide the first gastrocnemius recession described to this point in the surgical procedure). By limiting the travel of scalpel 44 through each of guides 46, depth guides limit the depth of the incision made by scalpel 44 to effect incision of the facial layer of the respective muscle. Referring to FIGS. 3 and 6, depth guides in the form of ramps 48g are positioned intermediate adjacent pairs of guides 46g on gastrocnemius retractor 28. In the exemplification shown, gastrocnemius retractor 28 includes two ramps 48g, with each ramp 48g extending from one of the walls forming a guide 46g.

Each ramp 48g is provided to cooperate with a scalpel 44f having flange 50 extending outwardly from its blade. Flange 50 is sized and positioned such that positioning of the blade of scalpel 44f into one of guides 46g causes flange 50 to abut at least one of ramps 48g to limit the travel of the blade of scalpel 44f through the chosen guide 46g and thereby limit the length of the blade of scalpel 44f that can extend through the chosen guide 46 and thereby also limit the depth of the incision into the fascial layer of gastrocnemius G that can be made.

Ramps 48g extend toward soleus retractor 26 and away from the gastrocnemius contacting side of gastrocnemius retractor 28 and, in the exemplification illustrated, taper from lateral to medial when the instrument is operably positioned to facilitate an intramuscular fascial lengthening to relieve equinus as described in this document. Stated another way, ramps 48g taper from a maximum height closest to first handle 30 to a minimum height farthest from first handle 30. In the surgical procedure of the present disclosure, flange 50 of scalpel 44f will, in the step of making a gastrocnemius recession to effect an intramuscular fascial lengthening to relieve equinus, first encounter a larger height of a ramp 48g and, as the incision is extended medially, will subsequently encounter progressively shorter portions of ramp 48g as ramp 48g tapers medially.

In the illustrated embodiment, depth guides take the form of ramps tapering along their length. In alternative configurations, the depth guides may take the form of guides extending a consistent height along their length. While flange 50 is illustrated in FIG. 8 as being positioned orthogonal to the longitudinal axis of scalpel 44, scalpel 44 may incorporate a guide surface/flange presenting a surface for contacting the retractor depth guide at an angle relative to the longitudinal axis of scalpel 44. Particularly, the guide contact surface of scalpel 44 may form an angle to the longitudinal axis of scalpel 44 that is substantially equal to the angle of the handle of scalpel 44 relative to the retractor being used to guide scalpel 44 during a recession.

In alternative forms of the present disclosure, a blocking instrument may be utilized in lieu of the guides described herein to limit the depth of incision. In these alternatives, a thin flexible sheet is inserted in the interval between the fascia and the underlying muscle. The sheet is not susceptible to penetration by the scalpel and; therefore, the sheet limits the depth of incision to the fascia.

During gastrocnemius recession, it can be important to incise the intermuscular septum between the medial and lateral heads of the gastrocnemius muscle. If present, the plantaris muscle is identified and should be released as well.

At this point in the surgical procedure, angle joint dorsiflexion is checked with the knee extended and the foot supinated. If ankle joint dorsiflexion is greater than 5 degrees with the knee extended (less than 85 degrees relative to the distal leg), then no further release is required. If ankle dorsiflexion is less than 5 degrees (more than 85 degrees relative to the distal leg), then a second recession of the gastrocnemius facial layer approximal one centimeter proximal to the first recession is performed. More particularly, the distal most guide 46g is utilized to guide the first gastrocnemius recession. With each of guides 46g being spaced approximately one centimeter from one or more adjacent guides 46g (and all of guides 46g being nominally parallel along their lengths), the next most proximal guide 46g may be utilized to facilitate a second gastrocnemius recession in the same manner as described above with respect to the first recession. Guides 46 on each retractor paddle are spaced a non-adjustable distance from the next adjacent guide(s) along their lengths, i.e., the spacing of adjacent guides 46 from each other is established at a set value that is not adjustable by actuation of instrument 24. The surgical procedure continues, with the third and final guide 46g being utilized to facilitate a third gastrocnemius recession if the second recession does not yield the desired ankle joint dorsiflexion.

When performing gastrocnemius recession, the scalpel is oriented with the blade positioned posterior of the scalpel handle to allow incision of the facial layer of the gastrocnemius G which is anatomically posterior to the soleus S. If soleus recession is also desired, a similar procedure to that described above with respect to the gastrocnemius can be performed. Specifically, with instrument 24 positioned with soleus retractor 26 spaced from gastrocnemius retractor 28 as illustrated in FIG. 8, guides 46s may be utilized to guide recession of the soleus S in the same manner described above with the gastrocnemius G. Specifically, scalpel 44 may be inserted in a generally posterior to anterior direction, with the scalpel blade being anterior to the scalpel handle and positioned within one of guides 46s and thereafter drawn from lateral to medial to incise the soleus S facial layer from lateral to medial in a direction substantially parallel to a transverse anatomical plane. Up to 3 soleus recessions can be made utilizing the instrument of the present disclosure, with each guide 46s spaced one centimeter from the adjacent guide or guides. Ankle joint dorsiflexion can be checked after each soleus recession as described with respect to each gastrocnemius recession.

Soleus retractor 26 may incorporate a depth guide positioned to cooperate with scalpel 44f to limit the travel of scalpel 44f through each of guides 46s to limit the depth of the incision made by scalpel 44 to effect incision of the facial layer of the respective muscle. Specifically, ramps 48s are structured and arranged to function in the same way as ramps 48g described in detail above. Therefore, a detailed description of ramps 48s is omitted for the sake of brevity.

In one form of the present disclosure, recession of either the gastrocnemius or soleus, as the case may be, can be visualized through respective gastrocnemius retractor 28 and soleus retractor 26. In one form of the present disclosure, such visualization may be done through open spaces 52 positioned on either side of guides 46. In a further alternative embodiment illustrated in FIG. 11, each of gastrocnemius retractor 28 and soleus retractor 26 do not include open spaces 52 but rather are formed of a transparent material through which visualization of a recession facilitated by instrument 24 can be visualized.

As illustrated in FIG. 1, gastrocnemius retractor 28 may be chosen from one of a plurality of gastrocnemius retractors 28a, 28b, and 28c. The plurality of gastrocnemius retractors are selectively securable to retractor head 22 by, e.g., a flexible detent mechanism. As illustrated in FIG. 1, each gastrocnemius retractor 27a, 28b, and 28c features a different length measured from medial to lateral in the operative position of instrument 24. Providing a plurality of gastrocnemius retractors 28 of differing lengths, allows the surgeon to choose the appropriate retractor based on patient physiology. Particularly, if the outer layer of skin through which incision 20 is made is spaced further from the gastrocnemius and soleus due to, e.g., the weight of the patient, then a longer gastrocnemius retractor can be chosen. A plurality of soleus retractors can similarly be provided to account for differing patient physiology.

When describing retractor head 22 of the present disclosure and, particularly, the gastrocnemius retractor and soleus retractor forming retractor head 22, particular ones of the retractor paddles extending from instrument 24 are identified with the muscle against which the paddle will be positioned in the surgical technique of the present disclosure. Specifically, "gastrocnemius retractor 28" and "soleus retractor 26" are identified. It will be apparent to a person having ordinary skill in the art that each retractor 26, 28 may, in certain circumstances be associated with each of the relevant muscles, i.e., the gastrocnemius and soleus. Specifically, with a consistent medial surgical approach (i.e., using an incision formed in the medial aspect of the distal leg and inserting instruments from medial to lateral through the incision) and with a consistent distal orientation of first handle 30 and second handle 32 during the surgical procedure, the "gastrocnemius retractor" for the left leg with be the "soleus retractor" for the right leg, and the "soleus retractor" for the left leg will be the "gastrocnemius retractor" for the right leg. Similarly, the orientation of handles 30, 32 will control which retractor paddle is associated with which muscle. Particularly, the "gastrocnemius retractor" of retractor head 22, with handles 30, 32 positioned distally and with retractor head 22 operably positioned in the left leg, as illustrated in FIGS. 7 and 8, will become the "soleus retractor" if the instrument orientation is rotated 180 degrees about an anatomical frontal axis of the patient. Similarly, the "soleus retractor" will become the "gastrocnemius retractor" when the instrument is repositioned as described in the preceding sentence. Therefore, physical descriptions of the gastrocnemius retractor and soleus retractor will be understood to be interchangeable between these two elements of the present disclosure. For example, the interchangeable gastrocnemius retractors 27a, 28b, and 28c could also be identified as interchangeable soleus retractors. It is within the scope of the present disclosure for instrument 24 to feature both interchangeable gastrocnemius retractors and interchangeable soleus retractors.

FIGS. 11A-11E illustrate instrument 24' according to another exemplification of the present disclosure. Instrument 24' is identical to instrument 24 with the exception of guides 46'. Unlike guides 46, guides 46' do not define slots. Guides 46' do not capture the blade of scalpel 44, but rather provide a single guide surface against which the blade of scalpel can rest during an incision of the gastrocnemius or soleus. Particularly, the surgeon can apply a force to scalpel 44 in a proximal to distal direction to engage scalpel 44 with a guide 46' positioned distally of the blade during the lateral to medial travel that scalpel 44 undergoes during incision of the gastrocnemius or soleus in accordance with the present disclosure. Alternatively, the surgeon can apply a force to scalpel 44 in a distal to proximal direction to engage scalpel 44 with a guide 46' positioned proximally of the blade during the lateral to medial travel that scalpel undergoes during incision of the gastrocnemius or soleus. With scalpel 44 pressed against a guide 46' (either distally or proximally), guide 46' defines the trajectory of an incision made in the gastrocnemius or soleus. Depth guides in the form, e.g., of ramps extending from the facing surfaces of the retractor paddles of instrument 24' may be utilized to restrict the depth of such incisions, as described above with respect to instrument 24. Proximal surfaces of each guide 46' are spaced 1 centimeter from the proximal surface(s) of adjacent guide(s) 46'. Similarly, distal surfaces of each guide 46' are spaced 1 centimeter from the distal surface(s) of adjacent guide(s) 46'.

Figure 12B:
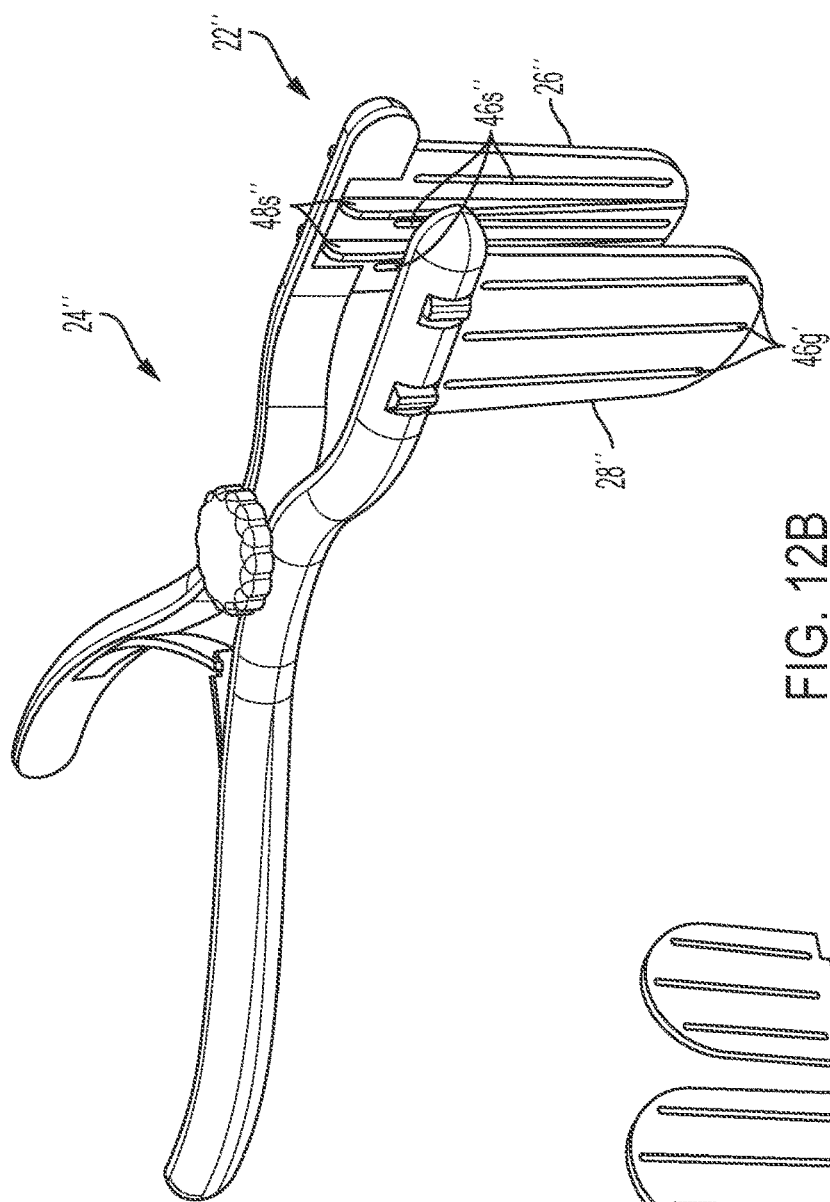
FIGS. 12A and 12B illustrate a further alternative embodiment instrument 24" in accordance with the present disclosure.
Figure 12A:
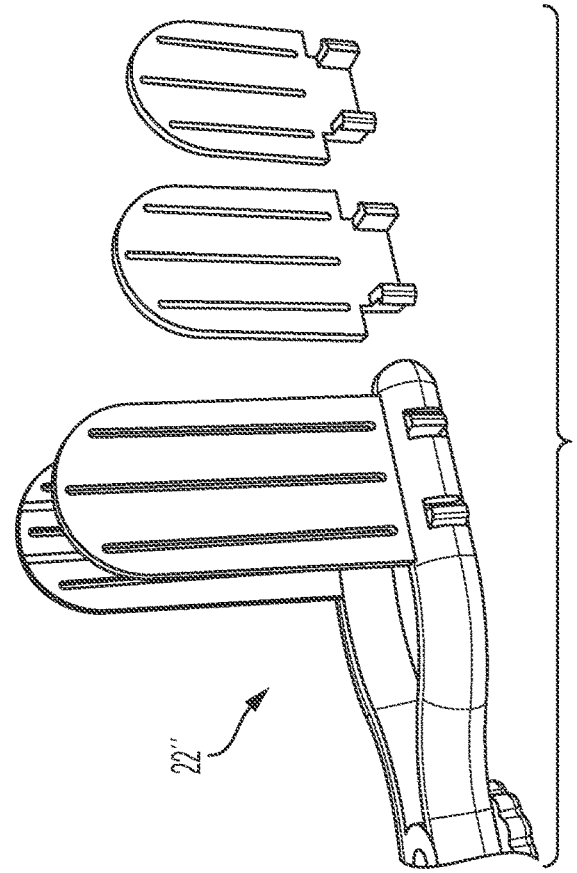

FIGS. 12A and 12B illustrate a further alternative instrument 24" according to another exemplification of the present disclosure. Unlike instruments 24 and 24', instrument 24" features retractor paddles 26, 28 that are solid, but for slots defining guides 46". Particularly, open spaces 52 do not form a part of retractor paddles 26, 28. In lieu of open spaces 52, gastrocnemius retractor 28 and soleus retractor 26 are transparent to allow for visualization therethrough.

Figure 13:
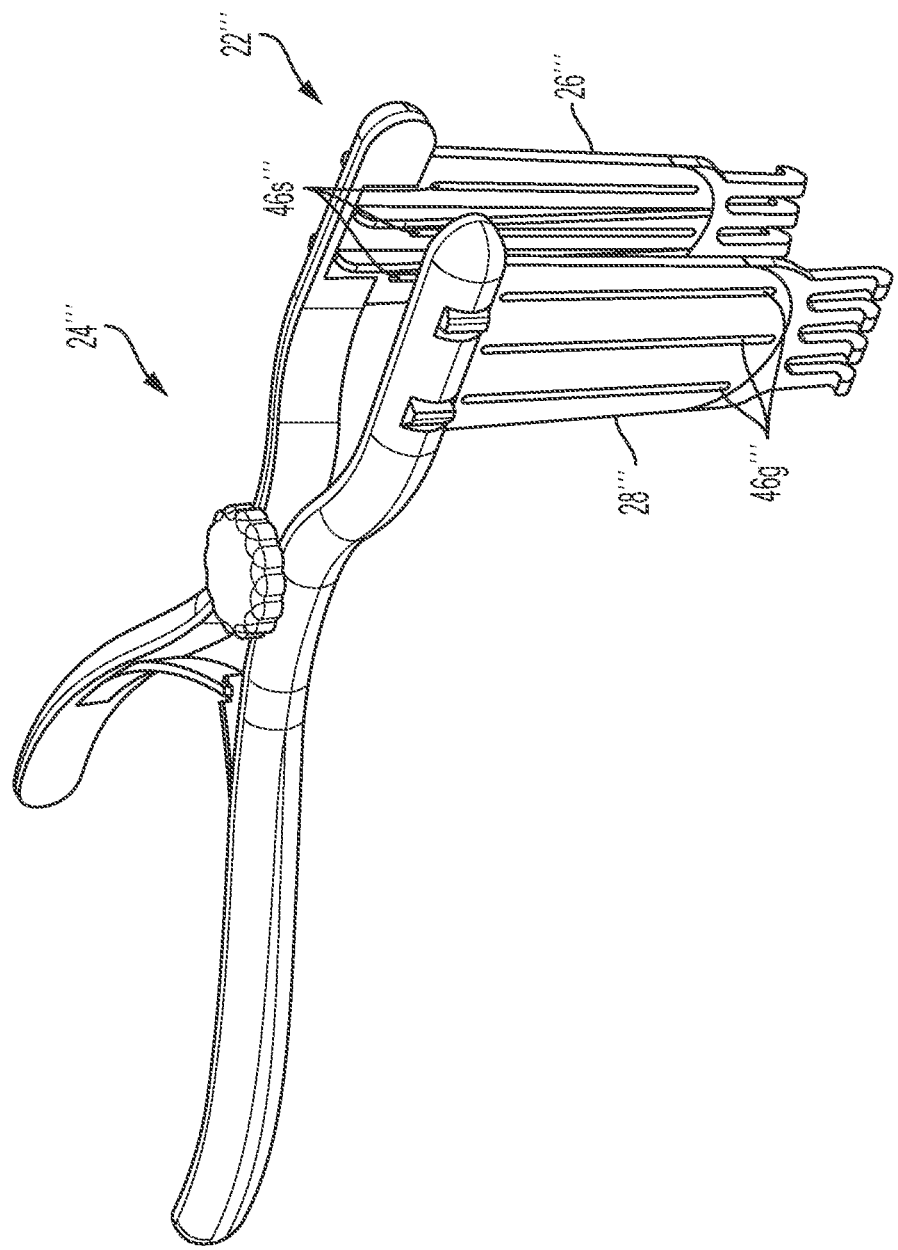
FIG. 13 illustrates an alternative embodiment instrument 24''' in accordance with the present disclosure.

FIG. 13 illustrates another alternative instrument 24' according to an alternative exemplification of the present disclosure. Unlike instruments 24, 24' and 24", instrument 24' features fingers extending from gastrocnemius retractor 28' and soleus retractor 26'''. Particularly, the fingers away from the handles of instrument 24''' and curve outwardly to provide the functionality of a Chung/Weitlander retractor as described above.

The various forms of instrument 24 may be formed of a molded thermoplastic and be designed as a single-use, disposable instrument. Alternatively, instrument 24 may be made of metal and may be a sterilizeable, multi-use instrument.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of relieving equinus, comprising:
   incising a patient's skin to provide an access to a gastrocnemius and a soleus of the patient;
   inserting an instrument into the access, the instrument comprising a retractor head, the retractor head comprising:
      a soleus retractor;
      a gastrocnemius retractor, the gastrocnemius retractor moveable relative to the soleus retractor over a range of motion from a closed position to an open position, the retractor head sized and shaped to be positioned in an interval between the gastrocnemius and the soleus in the closed position; and
      a plurality of spaced guides, a first one of the plurality of spaced guides maintaining a first position on the retractor head, a second one of the plurality of spaced guides maintaining a second position different from the first position on the retractor head;
   the inserting step further comprising inserting the retractor head into the access and into the interval between the gastrocnemius and the soleus;
   spacing the gastrocnemius from the soleus along a sagittal axis by opening the retractor head to space the soleus retractor from the gastrocnemius retractor, the first one of the plurality of spaced guides and the second one of the plurality of spaced guides positioned on the retractor head such that with the retractor head positioned by the inserting step and the spacing steps in a first position, the first one of the plurality of spaced guides is positioned to guide a first recession of one of the gastrocnemius and the soleus and the second one of the plurality of spaced guides is positioned to guide a second recession of one of the gastrocnemius and the soleus, the second recession spaced from the first recession;
   with the retractor head positioned by the inserting step and the spacing steps in the first position, guiding, with the first one of the plurality of spaced guides, the first recession of one of the gastrocnemius and the soleus to effect a first intramuscular fascial lengthening to relieve equinus; and
   with the retractor head maintaining the first position, guiding with a second one of the plurality of spaced guides a second recession of one of the gastrocnemius and the soleus to effect a first intramuscular fascial lengthening to relieve equinus, the second recession spaced from the first recession.

2. The method of claim 1, wherein the first one of the plurality of spaced guides is spaced along its length a non-adjustable distance from the second one of the plurality of spaced guides.

3. The method of claim 1, wherein the soleus retractor has a concave face opposite the gastrocnemius retractor, and the gastrocnemius retractor has a concave face opposite the soleus retractor, and wherein the inserting step further comprises the steps of:
   cupping the gastrocnemius with the gastrocnemius retractor; and
   cupping the soleus with the soleus retractor.

4. The method of claim 1, further comprising the step of:
   with the retractor head maintaining the first position, guiding with the second one of the plurality of spaced guides the second recession of the one of the gastrocnemius and the soleus to effect a second intramuscular fascial lengthening to relieve equinus.

5. The method of claim 4, wherein the first recession is spaced about 1 centimeter from the second recession.

6. The method of claim 4, further comprising the step of:
   guiding with a third one of the plurality of spaced guides a third recession to effect a third intramuscular fascial lengthening to relieve equinus.

7. The method of claim 6, wherein the second recession is spaced about 1 centimeter from the third recession.

8. The method of claim 4, wherein the first recession comprises a first gastrocnemius recession and the second recession comprises a soleus recession.

9. The method of claim 8, further comprising the steps of:
   guiding, with a third one of the plurality of spaced guides a second soleus recession to effect a third intramuscular fascial lengthening to relieve equinus, the second soleus recession spaced about 1 centimeter from the first soleus recession; and
   guiding with a fourth one of the plurality of spaced guides a third soleus recession to effect a fourth intramuscular fascial lengthening to relieve equinus, the second soleus recession spaced about 1 centimeter from the third soleus recession.

10. The method of claim 8, wherein the plurality of spaced guides comprises a plurality of spaced soleus retractor guides, and wherein each of said plurality of spaced soleus retractor guides comprises one of a plurality of spaced soleus retractor guide slots, each of said plurality of soleus retractor guide slots is sized to receive and guide a scalpel to effect a soleus recession to effect an intramuscular fascial lengthening to relieve equinus, a first one of said plurality of spaced soleus retractor guide slots sized to receive the scalpel to effect the first soleus recession.

11. The method of claim 10, wherein said soleus retractor further comprises a soleus retractor depth guide positioned to cooperate with the scalpel to limit the travel of the scalpel through each of the plurality of spaced soleus retractor guide slots to limit the depth of an incision made by the scalpel to effect a soleus recession.

12. The method of claim 11, wherein said soleus retractor depth guide comprises a ramp, the ramp positioned to abut a head of the scalpel to limit the travel of the scalpel through the retractor head to limit a depth of a muscle lengthening incision made by the scalpel to effect a soleus recession to a varying depth along a length of the muscle lengthening incision according to a variable height of each of the soleus retractor ramps.

13. The method of claim 8, further comprising the step of:
visualizing, through the soleus retractor, the step of guiding, with the first one of the soleus retractor guides, the first soleus recession to effect the first intramuscular fascial lengthening to relieve equinus.

14. The method of claim 13, wherein the soleus retractor comprises a substantially transparent soleus retractor material, and wherein said step of visualizing, through the soleus retractor, comprises the step of visualizing, through the substantially transparent soleus retractor material.

15. The method of claim 13, wherein the soleus retractor comprises a soleus retractor open space, and wherein said step of visualizing, through the soleus retractor, comprises the step of visualizing, through the soleus retractor open space.

16. The method of claim 8, wherein the soleus retractor comprises a first soleus retractor of a plurality of soleus retractors, the method further comprising the steps of:
selecting the first soleus retractor based on a physiology of the patient; and
securing the first soleus retractor to the retractor head before the inserting step.

17. The method of claim 1, wherein each of the plurality of spaced guides comprises one of a plurality of spaced guide slots, each of said plurality of guide slots sized to receive and guide a scalpel to effect a recession to effect an intramuscular fascial lengthening to relieve equinus, a first one of said plurality of spaced guide slots sized to receive the scalpel to effect the first gastrocnemius recession.

18. The method of claim 1, wherein the gastrocnemius retractor further comprises a plurality of depth guides positioned to cooperate with a scalpel to limit the travel of the scalpel through each of the plurality of spaced guides to limit the depth of an incision made by the scalpel to effect a recession.

19. The method of claim 18, wherein each of the plurality of depth guides comprises a ramp, the ramp positioned to abut a head of the scalpel to limit the travel of the scalpel through the retractor head to limit a depth of a muscle lengthening incision made by the scalpel to effect a recession to a varying depth along a length of the muscle lengthening incision according to a variable height of each of the ramps.

20. The method of claim 1, further comprising the step of:
visualizing, through at least one of the gastrocnemius retractor and the soleus retractor, the step of guiding, with the first one of the guides, the first recession to effect the first the intramuscular fascial lengthening to relieve equinus.

21. The method of claim 20, wherein at least one of the gastrocnemius retractor and the soleus retractor is formed of a substantially transparent material, and wherein said visualizing step comprises the step of visualizing, through the substantially transparent material, the step of guiding.

22. The method of claim 20, wherein at least one of the gastrocnemius retractor and the soleus retractor comprises an open space, and wherein said visualizing step comprises the step of visualizing, through the open space, the step of guiding.

23. The method of claim 1, wherein the gastrocnemius retractor comprises a first gastrocnemius retractor of a plurality of gastrocnemius retractors, the method further comprising the steps of:
selecting the first gastrocnemius retractor based on a physiology of the patient; and
securing the first gastrocnemius retractor to the retractor head before the inserting step.

24. The method of claim 1, wherein the instrument further comprises a first handle and a second handle, the first handle moveably secured to the second handle, the soleus retractor extending from the first handle, the gastrocnemius retractor extending from the second handle, the method further comprising the step of using the first handle and the second handle to maintain the position of the instrument during the step of guiding, the first handle and the second handle extending one of distally and proximally away from the incision during the step of guiding.

25. A method of relieving equinus, comprising:
incising a patient's skin to provide an access to a gastrocnemius and a soleus of the patient;
inserting an instrument into the access, the instrument comprising a retractor head, the retractor head comprising:
a soleus retractor;
a gastrocnemius retractor, the gastrocnemius retractor moveable relative to the soleus retractor over a range of motion from a closed position to an open position, the retractor head sized and shaped to be positioned in an interval between the gastrocnemius and the soleus in the closed position, the soleus retractor having a first soleus retractor side facing the gastrocnemius retractor and a second soleus retractor side opposite the first soleus retractor side, the second soleus retractor side facing away from the gastrocnemius retractor, the gastrocnemius retractor having a first gastrocnemius retractor side facing the soleus retractor and a second gastrocnemius retractor side opposite the first gastrocnemius retractor side, the second gastrocnemius retractor side facing away from the soleus retractor, the second soleus retractor side defining a first concave face of the retractor head, the second gastrocnemius retractor side defining a second concave face of the retractor head; and
a plurality of spaced guides;
the inserting step further comprising inserting the retractor head into the access and into the interval between the gastrocnemius and the soleus while cupping the soleus with the first concave face of the retractor head and cupping the gastrocnemius with the second concave face of the retractor head;
spacing the gastrocnemius from the soleus along a sagittal axis by opening the retractor head to space the soleus retractor from the gastrocnemius retractor; and
guiding, with a first one of the plurality of spaced guides, a first recession of one of the gastrocnemius and the soleus to effect a first intramuscular fascial lengthening to relieve equinus.

\* \* \* \* \*